United States Patent
Ghosh et al.

(10) Patent No.: US 9,314,779 B2
(45) Date of Patent: Apr. 19, 2016

(54) METHOD OF MAKING A CATALYST AND CATALYST MADE THEREBY

(75) Inventors: Ashim Kumar Ghosh, Houston, TX (US); Neeta Kulkarni, Houston, TX (US); Pamela Lawyer Harvey, Missouri City, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 600 days.

(21) Appl. No.: 13/570,731

(22) Filed: Aug. 9, 2012

(65) Prior Publication Data

US 2014/0046109 A1 Feb. 13, 2014

(51) Int. Cl.
| | |
|---|---|
| *B01J 29/06* | (2006.01) |
| *C07C 2/66* | (2006.01) |
| *B01J 29/44* | (2006.01) |
| *B01J 37/04* | (2006.01) |
| *B01J 37/18* | (2006.01) |
| *C07C 2/86* | (2006.01) |
| *B01J 37/16* | (2006.01) |
| *B01J 35/00* | (2006.01) |
| *B01J 29/40* | (2006.01) |
| *B01J 29/89* | (2006.01) |
| *B01J 37/00* | (2006.01) |

(52) U.S. Cl.
CPC *B01J 29/44* (2013.01); *B01J 29/40* (2013.01); *B01J 29/89* (2013.01); *B01J 35/0006* (2013.01); *B01J 37/04* (2013.01); *B01J 37/16* (2013.01); *B01J 37/18* (2013.01); *C07C 2/66* (2013.01); *C07C 2/864* (2013.01); *B01J 37/0009* (2013.01); *B01J 2229/186* (2013.01); *B01J 2229/37* (2013.01); *B01J 2229/42* (2013.01); *C07C 2529/22* (2013.01); *C07C 2529/44* (2013.01); *C07C 2529/67* (2013.01); *C07C 2529/74* (2013.01); *Y02P 20/52* (2015.11)

(58) Field of Classification Search
USPC .............. 502/63, 64, 66, 68, 71, 85; 585/466, 585/467
See application file for complete search history.

(56) References Cited

U.S. PATENT DOCUMENTS

| | | | |
|---|---|---|---|
| 3,702,886 A | 11/1972 | Argauer et al. | |
| 4,152,364 A * | 5/1979 | Chu | 585/454 |
| 4,683,214 A | 7/1987 | Angevine et al. | |
| 5,726,114 A | 3/1998 | Chang et al. | |
| 6,872,866 B1 | 3/2005 | Nemeth et al. | |
| 7,060,864 B2 | 6/2006 | Ghosh et al. | |
| 7,304,194 B2 | 12/2007 | Ghosh et al. | |
| 7,368,410 B2 | 5/2008 | Ghosh et al. | |
| 7,576,026 B2 * | 8/2009 | Ghosh et al. | 502/77 |
| 2005/0143613 A1 | 6/2005 | Dakka et al. | |
| 2008/0176736 A1 | 7/2008 | Ghosh et al. | |
| 2008/0306317 A1 | 12/2008 | Ghosh et al. | |
| 2009/0036723 A1 | 2/2009 | Ghosh et al. | |
| 2010/0113850 A1 | 5/2010 | Ghosh et al. | |

OTHER PUBLICATIONS

International Search Report for International Application No. PCT/US2012/067521; International Filing Date Dec. 3, 2012; Date of Mailing Apr. 22, 2013; 4 pages.
Written Opinion of the International Search Report for International Application No. PCT/US2012/067521; International Filing Date Dec. 3, 2012; Date of Mailing Apr. 22, 2013; 11 pages.

* cited by examiner

*Primary Examiner* — Elizabeth Wood
(74) *Attorney, Agent, or Firm* — Cantor Colburn LLP (57) ABSTRACT

In an embodiment, a method of forming a catalyst can comprises: treating a detemplated pentasil zeolite material with a phosphorus-containing compound to form a phosphorus treated zeolite; combining a hydrogenating material, the phosphorus treated zeolite, and a binder material to form a mixture; forming the mixture into a shaped body, wherein the mixture is formed into the shaped body without the mixture being heat-treated; and calcining the shaped body to form the catalyst. Combining the hydrogenating material with the phosphorus treated zeolite and the binder material occurs prior to forming of the shaped body.

16 Claims, 5 Drawing Sheets

METHOD OF MAKING A CATALYST AND CATALYST MADE THEREBY

TECHNICAL FIELD

The present disclosure relates generally to a method of preparing catalysts for use in the alkylation of aromatic compounds.

BACKGROUND

Descriptions of unit, abbreviation, terminology, etc. used throughout the present disclosure are summarized in Table 1.

Aromatic compounds can be alkylated to form different alkylated aromatic products. One that has particular value is para-xylene (e.g., p-xylene). Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalysts, particularly over zeolite catalysts. In particular, ZSM-5 zeolite, zeolite Beta and silicoaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction.

Thermodynamic equilibrium compositions of ortho-, meta-, and para-xylenes can be around 25, 50, and 25 mole %, respectively, at a reaction temperature of 500° C.; though, such toluene methylation can occur over a wide range of temperatures. Para-xylene can be separated from mixed xylenes by a cycle of adsorption and isomerization. Byproducts such as $C_{9+}$ and other aromatic products can be produced by secondary alkylation of the xylene product.

Unfortunately, there are a number of technical hurdles for toluene methylation to be commercially successful. These include fast catalyst deactivation (e.g., catalyst activity declines to less than or equal to 50% of its initial level when operating at a conversion of greater than or equal to 50%, in a period of 7 days), low methanol selectivity (e.g., only about 40% methanol selectively involves in methylation reaction), and so on. Most of the catalysts, if not all, for toluene methylation show fast catalyst deactivation. Typically, toluene conversion declines with time on stream due to rapid coke formation on the catalyst. Catalyst deactivation is one of the most difficult technical hurdles to overcome for commercial use of toluene methylation.

Accordingly, a method of preparation of a para shape selective catalyst that has increased catalyst stability when used in aromatic alkylation reactions, such as toluene methylation is desirable.

BRIEF DESCRIPTION

Disclosed herein are methods of forming a catalyst for use in aromatic alkylation, the catalysts formed thereby, and methods of aromatic alkylation using the catalysts formed thereby.

In an embodiment, a method of forming a catalyst for use in aromatic alkylation, can comprise: treating a detemplated pentasil zeolite material with a phosphorus-containing compound to form a phosphorus treated zeolite; and combining a hydrogenating material, the phosphorus treated zeolite, and a binder material to form a mixture; forming the mixture into a shaped body, wherein the mixture is formed into the shaped body without the mixture being heat-treated; wherein the combining of the hydrogenating material with the phosphorus treated zeolite and the binder material occurs prior to or during the forming of the shaped body.

In an embodiment, a method of aromatic alkylation, comprises: contacting a stream comprising toluene with any of the above catalysts and alkylating the toluene to form para-xylene.

The above described and other features are exemplified by the following figures and detailed description.

BRIEF DESCRIPTION OF THE DRAWINGS

For a more complete understanding of the present application, reference is now made to the following descriptions taken in conjunction with the accompanying figures, in which.

DETAILED DESCRIPTION

TABLE 1

| abbreviation | description |
|---|---|
| < | less than |
| ≥ | greater than or equal to |
| Å | Angstrom |
| $cm^3$/min | cubic centimeter per minute |
| ° C. | degree Celsius |
| g | gram |
| h | hour |
| LOI | loss on ignition |
| $m^2$/g | meter squared per gram |
| mL | milliliter |
| mL/g | milliliters per gram |
| mTorr | milliTorr |
| psig | pound per square inch gauge |
| p-xylene | para-xylene |
| $PV_{total}$ | total pore volume |
| SA | specific (BET) surface area |

TABLE 1-continued

| abbreviation | description |
|---|---|
| SAR | silica to alumina (mole) ratio |
| wt % | weight percent |

The present disclosure is directed to a method of preparation of a para shape selective zeolite catalyst that has increased catalyst stability when used for producing dialkylated aromatics (e.g., for producing para-isomers of dimethylbenzene (p-xylene), ethyltoluene, diethylbenzene, and so on). Particularly, the catalyst can be used for producing para-xylene by reaction of toluene and methanol, hereinafter called toluene methylation. A selectivity of greater than or equal to 80% to be considered useful. Specifically, a method is described for making a hydrogenating material containing phosphorus treated zeolite catalyst. The method includes incorporation of a hydrogenating material such as platinum with a phosphorus treated zeolite catalyst prior to (e.g., just prior to) forming into a shaped catalyst (with binder) such that the hydrogenating material containing catalyst is not calcined or the hydrogenating compound is not decomposed before forming the catalyst into shaped body. The resulting zeolite catalyst has shape selective properties showing greater than 90% para-xylene selectivity (hereinafter p-xylene selectivity refers to % p-xylene in mixed-xylene) for toluene methylation reaction. Such catalyst shows stable catalyst performance showing little or no decline in toluene conversion with reaction time. For example, the catalyst can achieve greater than 95% para-xylene selectivity and can achieve greater than 9 mole % toluene conversion at about 100 hours-on-stream (HOS), specifically at 400 hours-on-stream, and more specifically at 700 hours-on-stream, under certain reaction conditions.

The zeolite can be any of a number of zeolites, where zeolites are crystalline aluminosilicates with three-dimensional framework containing silica ($SiO_4$) and alumina ($AlO_4$) tetrahedra and can be naturally occurring or synthesized. In general, the zeolite framework contains channels and interconnected voids or pores, which can be occupied by cations and water molecules. Depending on the size and geometry of the pores and channels, zeolites can be classified as small, medium, or large pore zeolites, and also as one, two, or three-dimensional pore structure zeolites. They can be naturally occurring or synthesized.

Structure directing templating agents such as tetraethylammonium ($TEA^+$), tetrapropylammonium ($TPA^+$) or other cations can be present in as-synthesized zeolite. The templating agent can be removed, for example, by heating the zeolite at a temperature of 400° C. to 600° C., such that the zeolite can be a detemplated and subsequently ion-exchanged. The zeolite can be $H^+$ or $NH_4^+$ form and can contain no or trace amounts of alkali metal such as Na. For example, the zeolite can contain 0.5 wt % or less $Na_2O$, more specifically, less than or equal to 0.05 wt % $Na_2O$ based on the total weight of the zeolite.

Zeolites can have a $SiO_2/Al_2O_3$ mole ratio (SAR) of, for example, 25 to 1,000, specifically 200 to 500, and more specifically 200 to 400.

The zeolite can be from a family of pentasil zeolites that contain five membered ring units or pentasil units in the framework structure. Such zeolites include ZSM-5, ZSM-11, ZSM-23, ferrierite, mordenite, and so on. Silicalite which contains an isotypic framework of ZSM-5 can also be included. Specifically, the zeolite can be a pentasil zeolite which contains 10-membered ring pore openings in the structure. Zeolites with the 10-membered pore openings are also known as medium pore zeolites. Examples of such pentasil zeolite containing 10-membered ring pore openings or medium pore are ZSM-5, ZSM-11, silicalite, etc.

The zeolite can be ZSM-5 or MFI (International Zeolite Association nomenclature of ZSM-5). The ZSM-5 zeolite has two-dimensional pore structure with straight channels (5.4 Å×5.6 Å) which are intersected by sinusoidal channels (5.1 Å×5.7 Å) with maximum diameter of about 9 Å at the intersection. The ZSM-5 zeolite catalysts and their preparation are described, for example, in U.S. Pat. No. 3,702,886. Such ZSM-5 zeolites are aluminosilicates that contain both silicon and aluminum in the crystalline structure. ZSM-11 is another pentasil aluminosilicate zeolite that is similar to ZSM-5.

The starting zeolite can be an $NH_4^+$ or $H^+$ form. It can optionally contain up to trace levels of other cations (wherein a trace level is less than or equal to 0.5 wt % based upon the total weight of the zeolite).

For example, to provide para-selective properties to the ZSM-5 zeolite or other zeolites, the zeolite can be modified by treating it with phosphorus-containing compounds, though any other compound that similarly modifies the zeolite structure to increase para-xylene selectivity is also contemplated. Such phosphorus-containing compounds can include, but are not limited to phosphonic, phosphinous, phosphorus and phosphoric acids, salts and esters of such acids and phosphorous halides, or combinations comprising at least one of the foregoing. In particular, phosphoric acid ($H_3PO_4$), phosphorus acid ($H_3PO_3$), and ammonium hydrogen phosphate (($NH_4)_2HPO_4$) can be used as the phosphorus-containing compound to provide a catalyst for aromatic alkylation or toluene methylation with shape selective properties to provide increased para-selectivity. The phosphorus-containing compound can also include other non-acid phosphorus-containing compounds, such as ammonium hydrogen phosphate (($NH_4)_2HPO_4$).

The modified zeolites can contain phosphorus (P) in an amount of 0.01 to 15 wt %, specifically 1 to 15 wt %, more specifically 6 to 12 wt % based on the total weight of the modified zeolite. The catalyst can contain more than 7 wt % phosphorus, based upon a total weight of the modified zeolite. The catalyst can contain 1 to less than 12 wt % phosphorus, based upon a total weight of the modified zeolite.

The phosphorus treatment of the zeolite can be carried out by various techniques, such as slurry evaporation, wet incipient methods, and/or spray-dry methods. In slurry evaporation, phosphorus can be incorporated into the zeolite by preparing a slurry of the zeolite and an aqueous solution of the phosphorus compound. Heating of the slurry can be used to facilitate treatment of the zeolite and to evaporate liquids. Heating of the slurry can occur at temperatures of greater than or equal to 25° C., specifically 70° C. to 100° C. The slurry can also be stirred or agitated during this step to ensure uniform treatment.

The evaporation of the liquid from the zeolite slurry can be alternatively, or additionally, achieved using a spray-dry technique. In the wet incipient method, an aqueous solution of the phosphorus compound is added, such as by spraying, to the dry zeolite without forming a slurry. The dry zeolite, which can be initially in the form of a powder, can be mixed with the phosphorus compound or its aqueous solution. Water can be added to the mixture of zeolite powder and phosphorus containing compound or its solution to facilitate uniform interaction between them.

The phosphorus treated zeolite can be calcined using a temperature profile, e.g., with a maximum temperature of 400° C. to 700° C. Optionally, the phosphorus zeolite can be heated at a temperature of 300° C. or higher prior to binding and then the zeolite can be bound with a suitable binder, as described, for example, in U.S. Pat. No. 7,368,410. Calcining can take place over time, typically several minutes to one hour or more, specifically 5 minutes to 3 hours, more specifically 30 minutes to 1.5 hours. Calcining can also take place by gradually increasing the temperature over time.

The phosphorus treated zeolite is then treated with a hydrogenating material. The hydrogenating material can comprise any of Group 10 transition metals and can include nickel, palladium, platinum, as well as other metals, and combinations comprising at least one of the foregoing. The metal of the hydrogenating material can be platinum. The hydrogenating material can be added to the catalyst as a hydrogenating metal compound (e.g., a hydrogenating metal salt) that readily dissolves in water. For example, when the metal is platinum, the platinum source can be any applicable platinum source such as chloroplatinic acid ($H_2PtCl_6 \cdot 6H_2O$), tetraamine platinum nitrate (($NH_3$)$_4$Pt($NO_3$)$_2$), or a combination comprising at least one of the foregoing.

The hydrogenating material is added to the phosphorus treated zeolite and the phosphorus treated zeolite is formed into the desired shape before the hydrogenating material is heat treated. In other words, once the hydrogenating material and phosphorus treated zeolite are combined, it is not calcined before being formed into a shaped body, thereby reducing the steps of the present process. For example, the hydrogenating material is decomposed by heat treatment only subsequent to the forming of the shaped body.

A binder material and/or water can be combined with the phosphorus treated zeolite and the hydrogenating material to form a mixture. The binder material can include inorganic oxide materials. The binder material can comprise an aluminum or silica containing material such as silica, alumina, clay, aluminum phosphate, silica-alumina, or combinations comprising at least one of the foregoing. The resulting catalyst can comprise up to 99 wt %, e.g., 1 to 99 wt %, specifically 10 to 50 wt % of a binder material based on the total weight of the catalyst.

A mixture comprising the hydrogenating material, the phosphorus treated zeolite, the binder material, and optionally water can be formed into a shaped body and calcined. For example, the hydrogenating material can be added to the phosphorus treated zeolite, the binder material, and optionally water, prior to the forming of the shaped body such that the hydrogenating material has not incurred a calcination step before the forming of the shaped body. The mixture comprising the hydrogenating material can be formed into the shaped body by various forming processes such as pelletizing, tabletting, extruding, and any other technique of forming a catalyst into a shape, as well as a combination comprising at least one of the foregoing processes. Examples of shaped bodies include, but are not limited to, spherical, cylindrical, pellet, and tablet. One specific example is 1/16 inch cylindrically shaped extrudate.

After forming into a shaped body, the catalyst is prepared for use. For example, the catalyst is heat treated (e.g., to dry, calcine, and/or activate the catalyst). Hence, the shaped body can be dried, passively and/or actively (e.g., via heat treatment).

Optionally, the catalyst can be calcined, e.g., at a temperature of 250° C. to 600° C., specifically, 280° C. to 530° C., for a period of 0.5 h to 10 h, specifically 1 h to 8 h, e.g., to decompose the hydrogenating metal salt. The heat treatment can be under air, $O_2$, $N_2$, or a combination comprising at least one of the foregoing. Under heat treatment in an $O_2$ containing environment the hydrogenating material can turn into metal oxide (e.g., PtO).

After formation of the catalyst into a shaped body (e.g., by extrusion), and optionally after calcination, the catalyst can be activated prior to using the catalyst for aromatic alkylation reaction. The activation of the catalyst can be through partial or near complete reduction of the hydrogenating material. The material can be present in catalyst as metal oxide, e.g., PtO, particularly when the catalyst is heated under $O_2$ or $O_2$-containing environment. Such catalyst activation can be accomplished by heating in an environment containing a reducing gas such as $H_2$, a mixture of light alkane(s), or combinations comprising one or more of the foregoing. Catalyst activation can occur at a temperature of greater than or equal to 250° C., specifically 300° C. to 600° C., specifically 450° C. to 550° C., e.g., for a period of 0.5 hours or longer, specifically 0.5 to 5 hours, more specifically 0.5 to 3 hours. The catalyst can be activated by first drying at a temperature of 100° C. to 250° C. for 0.5 to 3 hours under flow of a reducing gas of 50 to 500 cm$^3$/min and then heating at a temperature of 250° C. to 600° C. for 0.5 to 5 hours under flow of a reducing gas of 50 to 500 cm$^3$/min. The activation can occur at atmospheric pressure, or 50 psig, or 100 psig, or higher.

Optionally, the catalyst can be steamed prior to use for the catalytic reactions. The catalyst can be steamed at a temperature of 200° C. to 600° C., specifically 200° C. to 400° C., e.g., for a period of more than 0.5, e.g., a period of 1 h to 10 h, before using the catalyst in any reaction. The steaming can be carried out in-situ or ex-situ of the reactor. In some embodiments, the catalyst is steamed at mild temperatures. Methods for steaming at mild temperatures are described, for example, in U.S. Pat. No. 7,304,194.

The catalyst can be used, in general, for acid-catalyzed reactions such as aromatic alkylation, transalkylation, toluene disproportionation, etc. Particularly, the catalyst can be used for reactions producing dialkylated aromatics to yield p-isomer selectively such as p-xylene, p-ethyltoluene, p-diethylbenzene, etc. More particularly, the catalyst can be used for toluene alkylation with an alkylating agent such as methanol yielding p-xylene at greater than equilibrium concentration. The p-xylene selectivity can be greater than or equal to 80%, greater than or equal to 90% or greater than or equal to 95% or even higher. Not to be limited by theory, the increased concentration of p-isomer could result in from the shape selectivity of the catalyst. Although the present process of forming the catalyst is particularly described in relation to alkylation, it is believed that the process can be used to form other useful catalysts (e.g., catalysts useful in other catalytic reactions such as toluene disproportionation, hydrocracking, hydrocarbon reforming, etc.).

The catalyst, after activation, can be contacted with an appropriate feed under alkylation reaction conditions to carry out the aromatic alkylation. While the process disclosed herein has application to many other catalytic processes (e.g., including to other aromatic alkylation reactions), it is well suited for toluene methylation to produce p-xylene using the above described zeolite catalyst. Although much of the description herein can be directed to such toluene methylation, it will be readily understood by those skilled in the art that it is not solely limited to such use.

For example, the catalyst can be contacted with an appropriate feed of an aromatic hydrocarbon and an alkylating agent under alkylation reaction conditions to carry out aromatic alkylation. In aromatic alkylation an "alkylation feed" can be used, e.g., comprising aromatic compound and the alkylating agent. A gas co-feed can also be used, e.g., comprising reducing gas (such as hydrogen), an inert gas, or combinations comprising at least one of the foregoing. As used herein with respect to toluene methylation, the expression "methylation feed" is meant to encompass the feed of toluene and methanol.

In addition to any co-feed gas, optionally water (e.g., in the form of steam), can also be introduced into the reactor as co-feed along with the alkylation feed. The water or steam used for the alkylation or methylation reaction can be introduced, with or without hydrogen or inert gas as co-feed, with the alkylation feed to the reactor during the startup of the alkylation reaction, or it can be introduced subsequent to initial startup. In either case, liquid water can be added and vaporized prior to its mixing with co-feed gas (if any) and the alkylation feed. The use of water co-feed in aromatic alkylation is described, for example, in U.S. Pat. No. 7,060,864.

The reactor pressure for toluene methylation or other aromatic alkylation can vary, but typically ranges from 10 to 1,000 psig. Reactor temperatures can vary, but typically range from 400° C. to 700° C. Upon introduction of feed into the reactor, the catalyst bed temperature can be adjusted to a selected reaction temperature to effect a desired conversion. The temperature can be increased gradually at a rate of 0.1° C. to 10° C./min to provide the desired final reactor temperature. As used in the examples, reactor temperature refers to the temperature as measured at the inlet of the catalyst bed of the reactor.

The reaction can be carried out in a variety of different reactors that are commonly used for carrying out aromatic alkylation reactions. Single or multiple reactors in series and/or parallel can be suitable for carrying out the aromatic alkylation or toluene methylation reactions.

The resulting catalyst can achieve greater than 90%, specifically greater than 95% para-xylene selectivity where the catalyst can achieve stable toluene conversion. For example, the catalyst can achieve greater than 9 mole % toluene conversion after 100 hours. The catalyst can achieve said conversion and/or selectivity values for greater than 250 hours, specifically for greater than 400 hours, and even more specifically greater than 700 hours. Specifically, the resulting catalyst can achieve stable performance producing p-xylene in toluene methylation reaction.

The following examples are provided to illustrate the method of preparing the catalyst. The examples are merely illustrative and are not intended to limit methods made in accordance with the disclosure to the materials, conditions, or process parameters set forth therein.

EXAMPLES

The materials used in the following examples are described in Table 2. Unless specifically stated otherwise, the materials are used in their form as set forth in Table 2, and the quantities identified in the examples are based upon that form.

TABLE 2

| Material | Source |
| --- | --- |
| $NH_4$-ZSM-5 (SAR 308), Moisture 0.15 wt %[a] | Zeolyst |
| $NH_4$-Beta (SAR 21), Moisture 1.34 wt %[a] | Zeolyst |
| H-Beta (SAR 215), Moisture 0.96 wt %[a] | Zeolyst |
| $NH_4$-Mordenite (SAR 18), Moisture 0.82 wt %[a] | Zeolyst |
| $NH_4$-Mordenite (SAR 88), Moisture 0.80 wt %[a] | Zeolyst |
| $NH_4$-Ferrierite (SAR 59), Moisture 0.33 wt %[a] | Zeolyst |
| Phosphoric acid ($H_3PO_4$), 85 wt % in aqueous | Sigma-Aldrich |

TABLE 2-continued

| Material | Source |
| --- | --- |
| Alumina (Pseudobohemite type), HiQ 10-S, LOI* 25 wt % | BASF |
| Nitric acid ($HNO_3$), ACS Reagent, 70 wt % in aqueous | Sigma-Aldrich |
| Chloroplatinic acid hexahydrate ($H_2PtCl_6 \cdot 6H_2O$), ≥37.50 wt % Pt | Sigma-Aldrich |
| Tetraamine platinum nitrate, $(NH_3)_4Pt(NO_3)_2$, 49.9 wt % Pt | Sigma-Aldrich |
| Toluene, 99.9 wt % purity | Fisher Chemical |
| Methanol, 99.9 wt % purity | Fisher Chemical |
| Hydrogen, 99.999 mole % purity | Air Liquide |
| Water, Deionized (DI) | SABIC lab |

[a]Free Moisture at 110° C., 16 hours
*Weight loss at 900° C.

Catalysts A, B, C, and D as described below were prepared by using a phosphorus treated ZSM-5 zeolite. The starting zeolite was a detemplated ammonium exchanged ZSM-5 ($NH_4$—ZSM-5) zeolite powder having a $SiO_2/Al_2O_3$ mole ratio (SAR) of 308 (Sample 1, Table 3). The $NH_4$—ZSM-5 zeolite powder was treated with phosphoric acid by adding the acid to the zeolite powder while mixing them together. Water was added to make the zeolite powder homogeneously moist. The weight ratio (as-is basis) of Zeolite:$H_3PO_4$:$H_2O$ was 1.00:0.48:0.04. The phosphorus treated ZSM-5 zeolite was then calcined using a programmed temperature profile with a max temperature of 530° C. for about 2 to 3 hours (Sample 2, Table 3). The phosphorus treated ZSM-5 (Sample 2, Table 3) was used for preparing Catalysts A, B, C, and D as described below.

Comparative Catalyst A (Pt/P—ZSM-5)

Comparative Catalyst A was prepared by impregnating the P—ZSM-5 zeolite powder with platinum (Pt) by wet-incipient method prior to binding it with alumina. Specifically, 0.62 g tetraamine platinum nitrate was dissolved in about 10 mL of deionized water to form a platinum-salt solution. The platinum-salt solution was added to 50.05 g P—ZSM-5 powder (Sample 2, Table 3) and mixed well. An additional 6 mL of water was sprayed onto the zeolite to make the zeolite powder moist homogeneously, and then calcined at 300° C. for 10 hours, resulting in Pt/P—ZSM-5 (Sample 3, Table 3). The calcined Pt/P—ZSM-5 powder was formed into 1/16-inch extrudates by binding with alumina. Specifically, 12.3 g alumina (dehydrated basis) was first peptized by mixing with 3.57 g $HNO_3$, in which 49.18 g sieved (through an 80 mesh screen) Pt/P—ZSM-5 (Sample 3, Table 3) was added and mixed. By spraying 16 mL of water and mixing the zeolite-alumina was made into an extrudable paste and was extruded as 1/16-inch cylindrical shaped extrudate. The extrudate was calcined at 300° C. for a period of 10 h.

Catalyst B (Pt/P—ZSM-5)

Catalyst B was prepared by adding the platinum-containing compound, tetraamine platinum nitrate, during the catalyst extrusion. Specifically, 12.5 g alumina (dehydrated basis) was peptized by mixing with 3.576 g $HNO_3$, in which 50.09 g sieved (through an 80 mesh screen) P—ZSM-5 powder (Sample 2, Table 3) was added and mixed. 0.62 g tetraamine platinum nitrate was dissolved in 10.02 g $H_2O$ and the solution was added to the zeolite-alumina mixture. By spraying 6.6 g of water and mixing, the zeolite-alumina was made into an extrudable paste and was extruded as 1/16-inch cylindrical shaped extrudate. The extrudate was calcined at 300° C. for 10 hours (h). In other words, from the addition of the platinum-containing compound until forming the shaped extrudate, the mixture was not calcined.

Catalysts C and D

Catalysts C and D were prepared by adding the platinum-containing compound, chloroplatinic acid, during catalyst extrusion. Specifically, 17.5 g alumina (dehydrated basis) was peptized by mixing with 5.02 g $HNO_3$ (70 wt %) in which 70.01 g sieved (through an 80 mesh screen) P—ZSM-5 (Sample 2, Table 3) was added and mixed. 1.15 g of chloroplatinic acid hexahydrate was dissolved in 5.0 g $H_2O$ and the solution was added to the zeolite-alumina mixture. By spraying about 21 g of water and mixing, the zeolite-alumina was made into an extrudable paste and was extruded as 1/16-inch cylindrical shaped extrudate. The extrudate was divided into two parts, one part was calcined at 300° C. for 10 h and the other part was calcined at 530° C. for 10 h, and the calcined samples are Catalysts C and D, respectively. Again, heat treatment between mixing the platinum compound and the zeolite to forming the shaped extrudate was avoided.

Specific BET surface area (SA) and total pore volume ($PV_{total}$) of Catalysts A, B, C, and D are shown in Table 3, where the specific surface area was calculated using the BET method, and $PV_{total}$ was calculated from the $N_2$ uptake at P/Po=0.99. Multi-point $N_2$ sorption was done at liquid $N_2$ temperature (−196° C.) at P/Po 0.03 to 0.99. The catalyst samples were degassed under vacuum <20 mTorr at 300° C. Elemental analysis of the catalysts was performed by X-ray fluorescence and wt % of Si, Al, P, and Pt (dry-basis) are included in Table 3.

As shown in Table 3, the P—ZSM-5 zeolite contained 35.96 wt % Si, 0.23 wt % Al, and 9.11 wt % P, had a specific BET surface area of 182 $m^2/g$ and a $PV_{total}$ of 0.12 mL/g Both the specific BET surface area and total pore volume of P—ZSM-5 decreased significantly with the phosphorus treatment of the ZSM-5 zeolite powder.

TABLE 3

| sample | prepared from sample | description | catalyst | composition, wt % Si | Al | P | Pt | SA ($m^2/g$) | $V_{total}$ (mL/g) |
|---|---|---|---|---|---|---|---|---|---|
| 1 | parent | $NH_4$-ZSM-5, SAR 308[a] | | 47.16 | 0.29 | NA | NA | 376 | 0.23 |
| 2 | 1 | P-treated ZSM-5 | | 35.96 | 0.23 | 9.11 | NA | 182 | 0.12 |
| 3 | 2 | P-ZSM-5 impregnated with Pt, calcined | | 35.22 | 0.27 | 8.69 | 0.71 | 173 | 0.12 |
| 4 | 3 | calcined Pt/P-ZSM-5, extruded | A | 27.39 | 11.10 | 6.91 | 0.51 | 177 | 0.15 |
| 5 | 2 | extruded, Pt downstream in the extruder | B | 27.64 | 10.74 | 6.99 | 0.51 | 172 | 0.14 |
| 6 | 2 | extruded, Pt downstream in the extruder | C | 27.55 | 10.80 | 6.86 | 0.64 | 192 | 0.15 |
| 7 | 2 | extruded, Pt downstream in the extruder | D | 27.98 | 10.63 | 7.02 | 0.63 | 192 | 0.15 |
| 8 | 2 | extruded P-ZSM-5 | E | 28.08 | 10.93 | 7.11 | NA | 185 | 0.14 |
| 9 | 1 | P-ZSM-5 impregnated with Pt, calcined | | 46.02 | 0.29 | NA | 0.54 | 383 | 0.23 |
| 10 | 9 | calcined Pt/ZSM-5, extruded | F | 35.91 | 10.65 | NA | 0.51 | 370 | 0.27 |
| 11 | 1 | extruded, Pt downstream in the extruder | G | 37.08 | 10.95 | NA | 0.52 | 368 | 0.27 |
| 12 | parent | $NH_4$-Beta zeolite, SAR 21 | | 40.31 | 3.63 | NA | NA | 442 | 1.12 |
| 13 | 12 | Beta zeolite, treated with $H_3PO_4$ | | 33.29 | 3.05 | 7.77 | NA | 229 | 0.74 |
| 14 | 13 | extruded, Pt downstream in the extruder | H | 25.10 | 14.54 | 5.83 | 0.54 | 223 | 0.40 |
| 15 | parent | H-Beta zeolite, SAR 215 | | 43.70 | 0.39 | NA | NA | 503 | 0.57 |
| 16 | 15 | Beta zeolite, treated with $H_3PO_4$ | | 36.92 | 0.32 | 7.37 | NA | 107 | 0.39 |
| 17 | 16 | extruded, Pt downstream in the extruder | I | 27.83 | 10.93 | 5.38 | 0.52 | 154 | 0.30 |
| 18 | parent | NH4-Mordenite zeolite, SAR 18 | | 39.56 | 4.14 | NA | NA | 350 | 0.33 |
| 19 | 18 | treated with $H_3PO_4$ | | 32.00 | 3.42 | 9.11 | NA | 7 | 0.07 |
| 20 | 19 | bound (not extruded), Pt added | J | 26.25 | 14.29 | 5.64 | 0.58 | 37 | 0.17 |
| 21 | parent | H-Mordenite zeolite, SAR 88 | | 43.82 | 0.96 | NA | NA | 442 | 1.12 |
| 22 | 21 | treated with $H_3PO4$ | | 36.73 | 0.80 | 7.33 | NA | 24 | 0.10 |
| 23 | 22 | extruded, Pt downstream in the extruder | K | 28.72 | 11.37 | 5.51 | 0.54 | 113 | 0.20 |
| 24 | parent | $NH_4$-Ferrierite zeolite, SAR 59 | | 43.19 | 1.41 | NA | NA | 307 | 0.67 |
| 25 | 24 | Ferrierite zeolite, treated with $H_3PO_4$ | | 36.30 | 1.20 | 6.92 | NA | 188 | 0.320 |
| 26 | 25 | extruded, Pt downstream in the extruder | L | 29.01 | 11.38 | 5.56 | 0.50 | 181 | 0.33 |

[a]Parent $NH_4$-ZSM-5 contains <0.05 wt % $Na_2O$;

NA = not applicable, that is, sample contains no P or Pt

Pt source for Sample 6 and 7 prep was $H_2PtCl_6 \cdot 6H_2O$;

Pt source for all other prep was $(NH_3)_4Pt(NO_3)_2$

Comparative Catalysts
Catalyst E (P—ZSM-5)

Comparative Catalyst E is a phosphorus treated ZSM-5 alumina bound catalyst containing no hydrogenating metal. The phosphorus treated ZSM-5 (P—ZSM-5) (Sample 2, Table 3) zeolite was sieved through an 80 mesh screen and was extruded as follows: 15.01 g $Al_2O_3$ (dehydrated basis) was treated with 4.29 g $HNO_3$ and 60.04 g P—ZSM-5 zeolite powder was mixed with alumina. An additional 26 mL of water was added to the zeolite-alumina mixture and the mixture was extruded into 1/16 inch extrudate. The extrudate was calcined at 530° C. for 10 h.

Catalyst F (Pt/ZSM-5)

Comparative Catalyst F is an alumina bound Pt containing ZSM-5 that was not treated with phosphorus compound. The starting material was a $NH_4$—ZSM-5 powder having a $SiO_2/Al_2O_3$ mole ratio of 308 (Sample 1, Table 3). The ZSM-5 zeolite was impregnated with platinum by the wet-impregnation method. 0.624 g of platinum salt (tetraamine platinum nitrate) was dissolved in 10 mL of water, and the solution was sprayed on 50.07 g zeolite powder. An additional 16 mL of water was added to the zeolite and mixed, then calcined at 300° C. for 10 h. The Pt/ZSM-5 powder (Sample 9, Table 3) was sieved through an 80 mesh screen and was bound with alumina as binder (20%) and extruded to form 1/16 inch extrudates as follows: 12.3 g $Al_2O_3$ (dehydrated basis) was treated with 3.74 g $HNO_3$ and 49.04 g sieved Pt/ZSM-5 zeolite powder was mixed with alumina. About 24 mL of water was additionally added to the zeolite-alumina mixture and the mixture was extruded into 1/16 inch extrudate. The extrudate was calcined at 300° C. for 10 h.

Catalyst G (Pt/ZSM-5)

Comparative Catalyst G is an alumina bound Pt containing ZSM-5 that was not treated with phosphorus compound and platinum was added to zeolite during extrusion. The starting material was a $NH_4$—ZSM-5 powder having a $SiO_2/Al_2O_3$ mole ratio of 308 (Sample 1, Table 3). Platinum was incorporated in the ZSM-5 catalyst during extrusion of $NH_4$—ZSM-5 powder with alumina. Specifically, 0.620 g of platinum salt (tetraamine platinum nitrate) was dissolved in 10.1 of mL water. 12.51 g $Al_2O_3$ (dehydrated basis) was treated with 3.82 g $HNO_3$ and 50.05 g $NH_4$—ZSM-5 zeolite powder was mixed with alumina. Platinum salt solution was sprayed to zeolite-alumina while mixing. About 10.3 of mL water was additionally added to the zeolite-alumina mixture and the mixture was extruded into 1/16 inch extrudate. The extrudate was calcined at 300° C. for 10 h.

Catalyst H (Pt/P-Beta)

Comparative Catalyst H is an alumina bound platinum containing phosphorus treated Beta zeolite having a $SiO_2/Al_2O_3$ mole ratio of 21, where platinum was added to zeolite during extrusion. The starting material was a $NH_4$-Beta zeolite powder (Sample 12, Table 3). The Beta zeolite was first treated with a phosphorus compound and then extruded with alumina as binder, and platinum was added while extruding. 100.01 g Beta zeolite, 34.29 g $H_3PO_4$ acid and 90 mL water were mixed homogeneously and then the mixture was calcined at 530° C. for 10 h. The phosphorus treated Beta zeolite (P-Beta, Sample 13, Table 3) was sieved through an 80 mesh screen and was extruded as follows: 0.622 g of platinum salt (tetraamine platinum nitrate) was dissolved in 10.0 mL of water. 12.52 g $Al_2O_3$ (dehydrated basis) was treated with 3.82 g $HNO_3$ and 50.09 g P-Beta zeolite powder was mixed with alumina. Platinum salt solution was sprayed to zeolite-alumina while mixing. An additional 28.6 mL of water was added to the zeolite-alumina mixture and the mixture was extruded into 1/16 inch extrudate. The extrudate was calcined at 300° C. for 10 h.

Catalyst I (Pt/P-Beta (215))

Comparative Catalyst I is an alumina bound platinum containing phosphorus treated Beta zeolite having a $SiO_2/Al_2O_3$ mole ratio of 215, where platinum was added to the zeolite during extrusion. The starting material was an H-Beta zeolite powder (Sample 15, Table 3). The Beta zeolite was first treated with a phosphorus compound and then extruded with alumina as binder, and platinum was added while extruding. Following components 150.05 g Beta zeolite, 51.44 g $H_3PO_4$ acid, and 102 mL of water were mixed homogeneously and then the mixture was calcined at 530° C. for 10 h. The phosphorus treated Beta zeolite (P-Beta, Sample 16, Table 3) was sieved through an 80 mesh screen and was extruded as follows: 0.624 g of platinum salt (tetraamine platinum nitrate) was dissolved in 10.0 mL of water, 12.65 g $Al_2O_3$ (dehydrated basis) was treated with 3.89 g $HNO_3$ and 50.62 g P-Beta zeolite powder was mixed with alumina, platinum salt solution was sprayed to zeolite-alumina while mixing, an additional 23.5 mL water was added to the zeolite-alumina mixture, and the mixture was extruded into 1/16 inch extrudate. The extrudate was calcined at 300° C. for 10 h.

Catalyst J (Pt/P-Mordenite (18))

Comparative Catalyst J is an alumina bound platinum containing phosphorus treated Mordenite zeolite having a $SiO_2/Al_2O_3$ mole ratio of 18, where platinum was added to zeolite during extrusion. The starting material was H-Mordenite zeolite powder (Sample 18, Table 3). The mordenite zeolite was first treated with a phosphorus compound and then extruded with alumina as binder, and platinum was added while extruding. Following components 150.14 g Mordenite zeolite, 51.47 g $H_3PO_4$ acid (85%), and 58 mL of water were mixed homogeneously and the mixture was calcined at 530° C. for 10 h. The phosphorus treated Mordenite zeolite (Sample 19, Table 3) was sieved through an 80 mesh screen and was extruded as follows: 0.74 g of platinum salt (tetraamine platinum nitrate) was dissolved in 10.0 mL of water. 15.02 g $Al_2O_3$ (dehydrated basis) was treated with 4.58 g $HNO_3$ and 60.02 g P-Mordenite zeolite powder was mixed with alumina. Platinum salt solution was sprayed to zeolite-alumina while mixing. An additional 22 mL of water was added to the zeolite-alumina mixture and the mixture was not extruded but formed into small chunks. The extrudate was calcined at 300° C. for 10 h.

Catalyst K (Pt/P-Mordenite 88)

Comparative Catalyst K is an alumina bound platinum containing phosphorus treated Mordenite zeolite having a $SiO_2/Al_2O_3$ mole ratio of 88, where platinum was added to the zeolite during extrusion. The starting material was H-Mordenite zeolite powder (Sample 21, Table 3). The Mordenite zeolite was first treated with a phosphorus compound and then extruded with alumina as a binder, and platinum was added during extruding. Following components 100.02 g Mordenite zeolite, 34.28 g $H_3PO_4$ acid (85%), and 62 mL of water were mixed homogeneously and then the mixture was calcined at 530° C. for 10 h. The phosphorus treated Mordenite zeolite (Sample 22, Table 3) was sieved through an 80 mesh screen and was extruded as follows: 0.62 g of platinum salt (tetraamine platinum nitrate) was dissolved in 10.0 mL of water, 16.70 g $Al_2O_3$ (dehydrated basis) was treated with 3.82 g $HNO_3$, and 50.08 g P-Mordenite zeolite powder was mixed with alumina, the platinum salt solution was sprayed to zeolite-alumina while mixing and an additional 25 mL of water was added to the zeolite-alumina mixture and the mixture was extruded into 1/16 inch extrudate. The extrudate was calcined at 300° C. for 10 h.

Catalyst L (Pt/P-Ferrierite (55))

Comparative Catalyst L is an alumina bound platinum containing phosphorus treated Ferrierite zeolite having a $SiO_2/Al_2O_3$ mole ratio of 59; where platinum was added to the zeolite during extrusion. The starting material was $NH_4$-Ferrierite zeolite powder (Sample 24, Table 3). $NH_4$-Ferrierite zeolite was first treated with a phosphorus compound and then extruded with alumina as a binder, and platinum was added during extrusion. Following components 150.04 g Ferrierite zeolite, 51.47 g $H_3PO_4$ acid, and 169 mL of water were mixed homogeneously and the mixture was calcined at 530° C. for 10 h. The phosphorus treated Ferrierite zeolite (Sample 25, Table 3) was sieved through an 80 mesh screen and was extruded as follows: 0.87 g of platinum salt (tetraamine platinum nitrate) was dissolved in 10.0 mL of water. 23.36 g $Al_2O_3$ (dehydrated basis) was treated with 5.35 g $HNO_3$ and 70.09 g P-Ferrierite zeolite powder was mixed with alumina. Platinum salt solution was sprayed to zeolite-alumina while mixing. Additional 66 mL of water was added to the zeolite-alumina mixture and the mixture was extruded into 1/16 inch extrudate. The extrudate was calcined at 300° C. for 10 h.

The elemental analyses and the specific BET surface areas and total pore volume of Comparative Catalysts E through L and their precursors were measured and are included in Table 3.

Catalytic Performance Test

Catalysts B through D and Comparative Catalysts A and E through L were tested for toluene alkylation with methanol (toluene methylation). Except for Comparative Catalyst J, all catalysts were 1/16-inch extruded catalysts, where Comparative Catalyst J was bound with alumina and formed into chunks. All catalysts were crushed and sieved to obtain 20-40 mesh sized catalyst materials for loading in a reactor. In each catalytic test experiment, a measured volume of sized catalyst (5.4 mL) was loaded in a tubular SS reactor, installed, and leak tested. In testing each catalyst containing platinum was activated by first drying at 200° C. for 1 hour under $H_2$ flow (200 cm$^3$/min) at atmospheric pressure, followed by heating under $H_2$ flow (840 cm$^3$/min) at 510° C. for 2 hours (activation method "A1"), heating under $H_2$ flow (840 cm$^3$/min) at 510° C. for 3 hours (activation method "A2"), or heating under $H_2$ flow (840 cm$^3$/min) at 510° C. for 2 hours 40 minutes (activation method "A3"), to reduce the hydrogenating material. One of the comparative catalysts, Comparative Catalyst E, containing no platinum was only dried at 200° C. under $H_2$ flow. Catalyst load, drying, and activation conditions are summarized in Table 4.

As used herein, catalytic activity can be expressed as the % moles of the hydrocarbon or reactant converted with respect to the moles of hydrocarbon or reactant fed. In toluene methylation where toluene is converted to xylenes, the catalytic activity can be measured by the toluene converted with respect to the moles of toluene fed and can be defined by the following formulas:

$$\text{mole \% toluene conversion} = [(T_i - T_o)/T_i] \times 100 \quad (1)$$

where: $T_i$ is the number of moles of toluene fed and $T_o$ is the number of moles toluene unreacted.

As used herein, selectivity for mixed xylenes can be expressed as:

$$\text{mole \% mixed xylene selectivity} = [X_t/(T_i - T_o)] \times 100 \quad (2)$$

where: $X_t$ is the number of moles of total or mixed (o-, m-, or p-) xylenes in the product. As used herein, selectivity for para-xylene can be expressed as:

$$\text{mole \% para-xylene selectivity} = (X_p/X_t) \times 100 \quad (3)$$

where: $X_p$ is the number of moles of para-xylene.
As used herein, methanol conversion can be expressed as:

$$\text{mole \% methanol conversion} = [(M_i - M_o)/M_i] \times 100 \quad (4)$$

where: $M_i$ is the number of moles of methanol fed and $M_o$ is the number of moles methanol unreacted.
As used herein, methanol selectivity for toluene methylation can be expressed as:

$$\text{mole \% methanol selectivity} = [X_t/(M_i - M_o)] \times 100 \quad (5)$$

TABLE 4

| | | Catalyst Load | | |
|---|---|---|---|---|
| Example | Catalyst | Volume, mL | Weight, g | Activation Method |
| 1 | A | 5.4 | 4.96 | A2 |
| 2 | B | 5.4 | 5.09 | A2 |
| 3 | C | 5.4 | 5.10 | A1 |
| 4 | D | 5.4 | 5.13 | A1 |
| 5 | E | 5.4 | 4.73 | None |
| 6 | F | 5.4 | 4.00 | A3 |
| 7 | G | 5.4 | 4.06 | A3 |
| 8 | H | 5.4 | 3.28 | A3 |
| 9 | I | 5.4 | 3.93 | A3 |
| 10 | J | 5.4 | 3.74 | A3 |
| 11 | K | 5.4 | 3.77 | A3 |
| 12 | L | 5.4 | 2.92 | A3 |

Toluene methylation feed was introduced at 510° C. after catalyst activation. The feed contained premixed toluene/methanol (4.5/1.0 molar ratio) (0.34 g/min) and $H_2$ (840 cm$^3$/min) and was introduced to the reactor. The liquid feed (containing toluene and methanol) was vaporized by passing through a coiled tubing heated at 200° C. The reactor inlet pressure was maintained at about 20 psig. No changes were made during the test run and the catalyst bed inlet temperature was maintained at 510° C. Thus, toluene conversion as a function of time on stream provided the catalyst deactivation profile.

Examples 1-4

Figure 1:
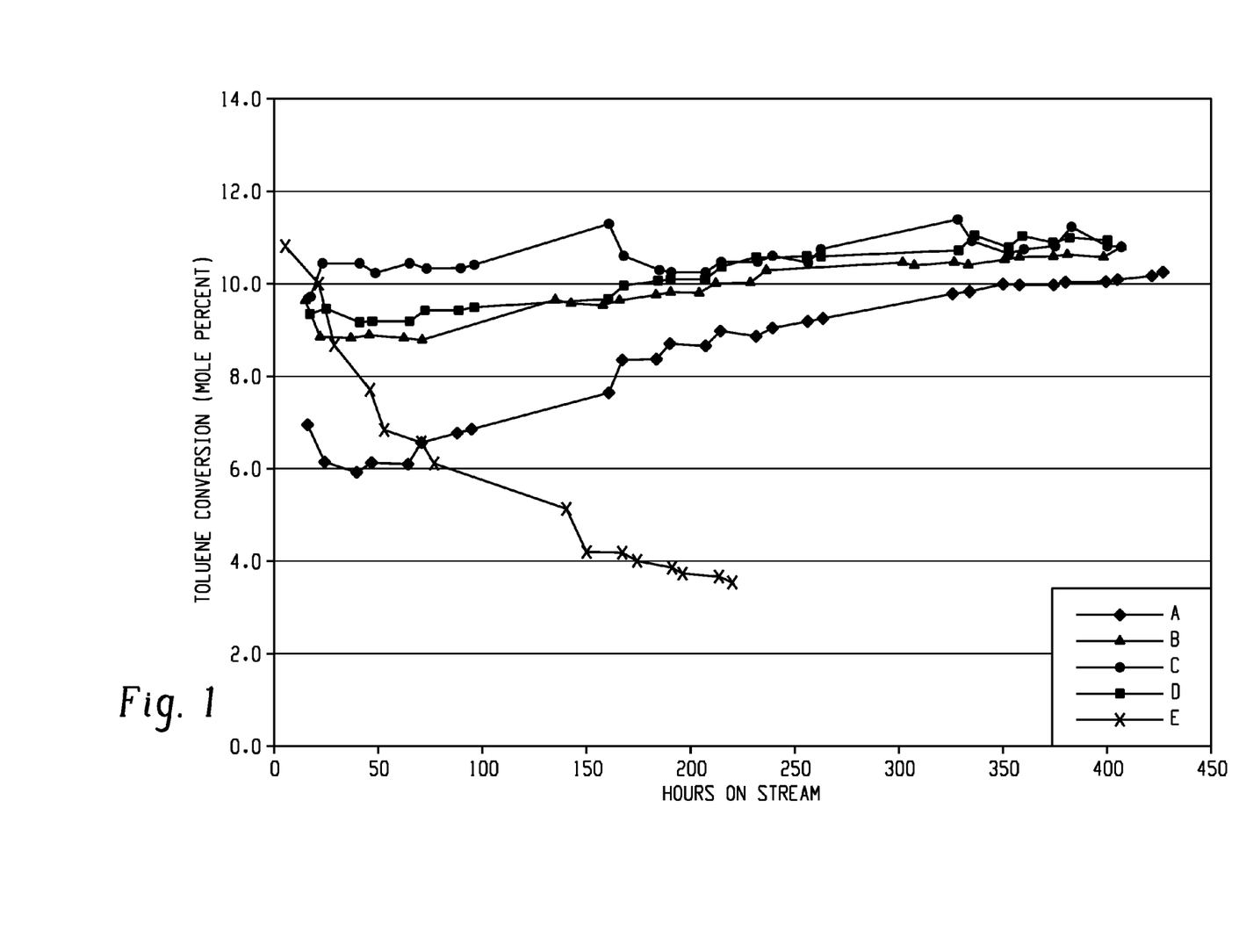
FIG. 1 shows a plot of toluene conversion with time on stream for toluene methylation reactions using Comparative Catalyst A, Catalysts B, C, and D, and Comparative Catalyst E.
Figure 2:
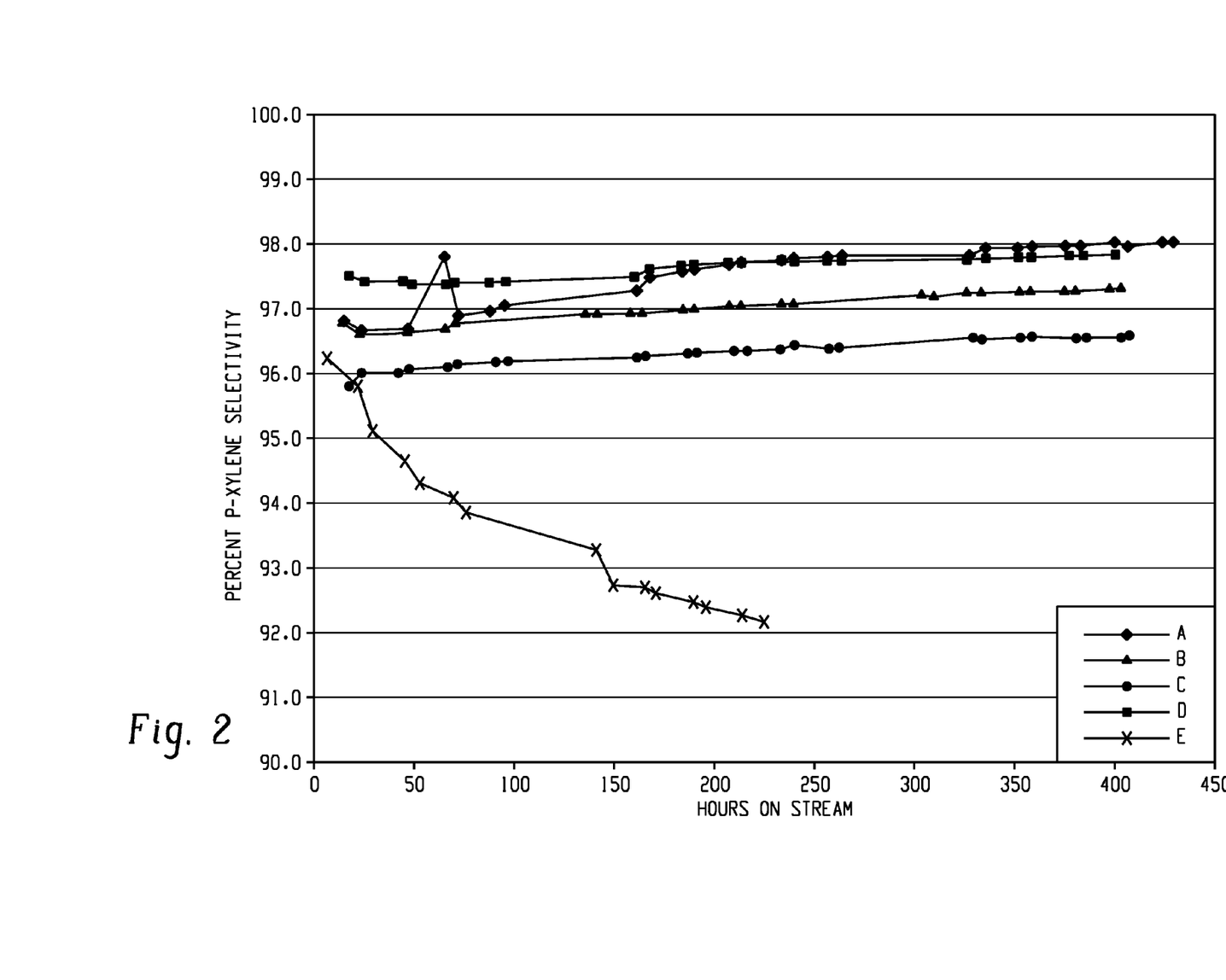
FIG. 2 shows a plot of para-xylene selectivity obtained using Comparative Catalyst A, Catalysts B, C, and D, and Comparative Catalyst E.

Comparative Catalyst A and Catalysts B-D were used in Examples 1-4. Catalytic performance data from Examples 1-4 are summarized in Table 5. FIGS. 1 and 2 show toluene conversions and p-xylene selectivity as a function of time on stream of Catalysts A, B, C, and D. Catalysts B, C, and D are Pt containing alumina bound P—ZSM-5 catalysts and Pt was added while extruding the phosphorus treated ZSM-5 zeolite powder. Whereas Comparative Catalyst A was made by first adding the platinum to the P—ZSM-5 powder which was then calcined resulting in Pt/P—ZSM-5, and then the calcined Pt/P—ZSM-5 powder extruded with alumina binder. The catalytic test data show that the Pt/P—ZSM-5 zeolite catalysts where Pt was added during extrusion resulted in an increase in conversion and did not reduce the selectivity.

Figure 3:
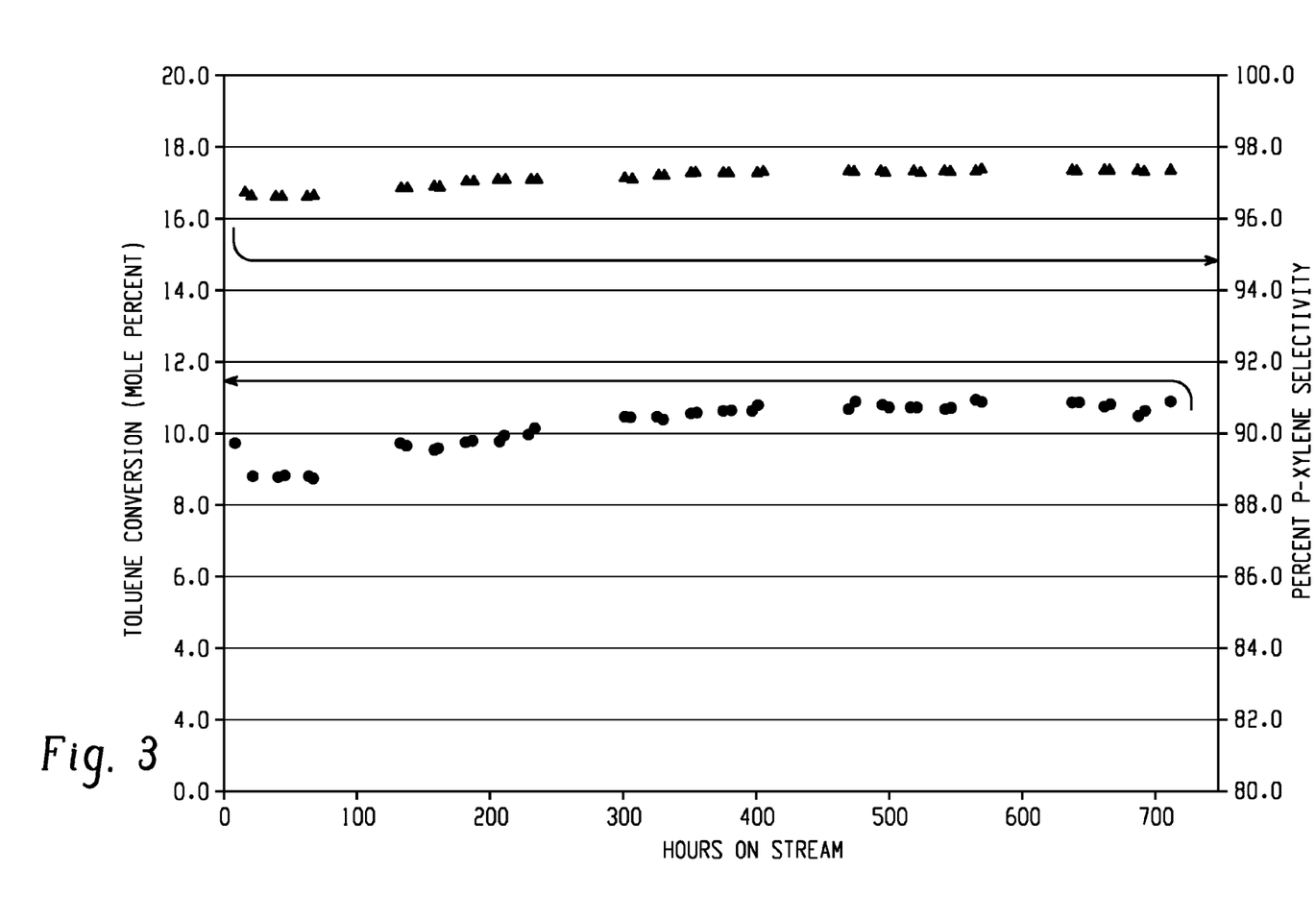
FIG. 3 shows a plot of toluene conversion and p-xylene selectivity with time on stream for toluene methylation reactions using Catalyst B.

FIG. 3 shows toluene conversions and p-xylene selectivity on Catalyst B (Example 2) where the catalyst was tested for about 30 days to show its stable performances after reaching steady-state.

Example 5

In Example 5, Comparative Catalyst E, containing no platinum, was tested after drying at 200° C. for 1 hour under $H_2$ flow (200 cm$^3$/min) at atmospheric pressure. Toluene methylation feed (premixed toluene-methanol, 0.34 g/min) and $H_2$ (840 cm$^3$/min) were introduced to reactor at 200° C. and catalyst bed temperature was ramped to 510° C., and reactor inlet pressure was adjusted and maintained at 20 psig. No changes made during the test run and the catalyst bed inlet temperature was maintained at 510° C. Toluene conversion and selectivity of Comparative Catalyst E is included in FIGS. 1 and 2.

Examples 6-12

Comparative Catalysts F, G, H, I, J, K, and L, each containing platinum, were used in Comparative Examples 6 through 12. Catalyst loads and test conditions are the same as those were used for Examples 1-4 described earlier and are summarized in Table 4, and catalytic results are summarized in Table 5.

Figure 4:
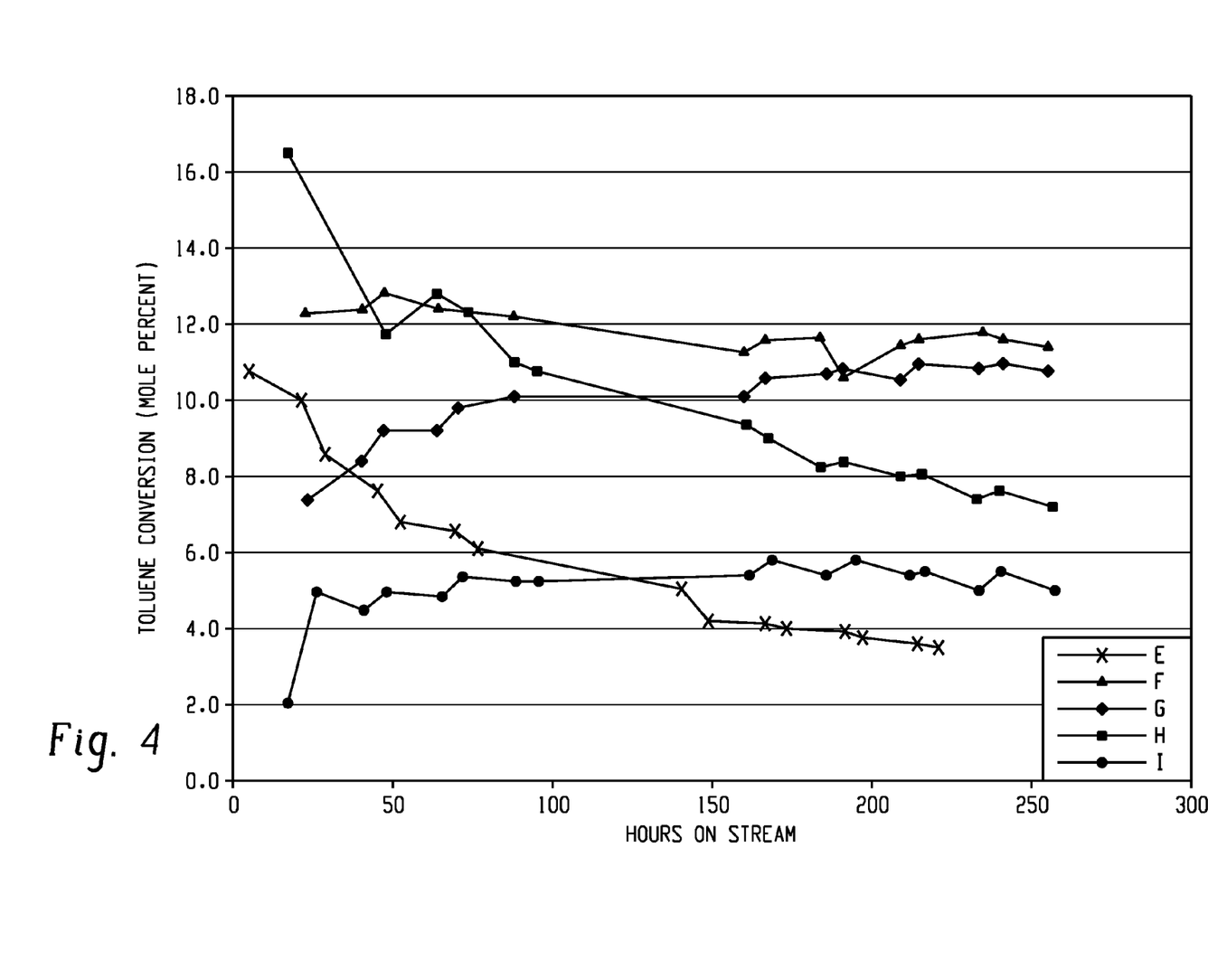
FIG. 4 shows a plot of toluene conversion with time on stream for toluene methylation reactions using Comparative Catalysts E through I.
Figure 5:
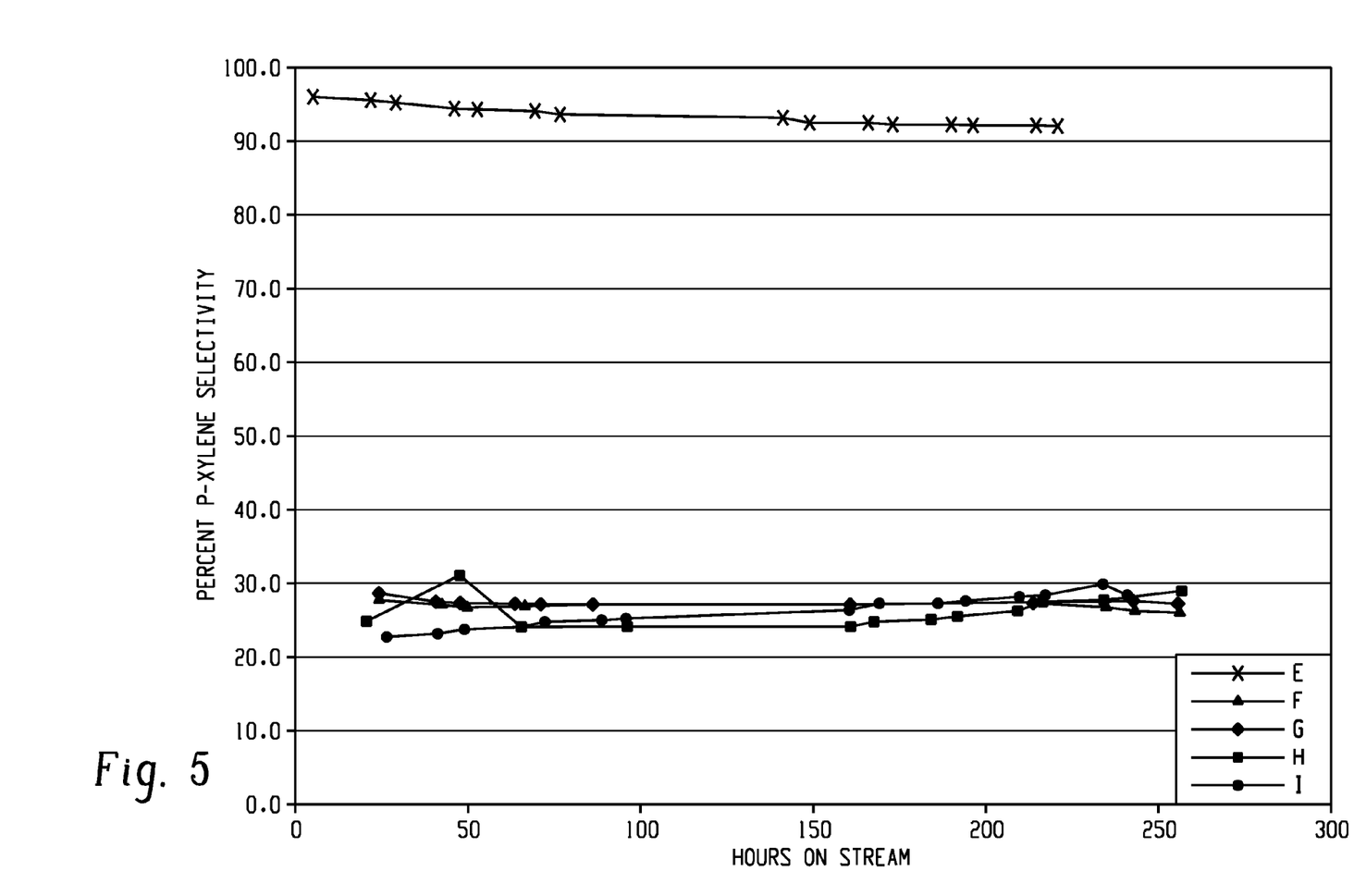
FIG. 5 shows a plot of p-xylene selectivity with time on stream for toluene methylation reactions using Comparative Catalysts E through I.

FIGS. 4 and 5 show toluene conversions and p-xylene selectivity as a function of time on stream on Comparative Catalysts E, F, G, H, and I. Comparative Catalysts J, K, and L showed no toluene conversions.

A $NH_4$—ZSM-5 zeolite (SAR 308) was used for making Catalysts B through D and Comparative Catalysts A and E through G. Catalysts A, B, C, and D are phosphorus treated ZSM-5 catalysts containing the hydrogenating material platinum, where platinum was added during extrusion for Catalysts B through D, and the platinum was added on the zeolite first, calcined and then extruded into shaped body for Comparative Catalyst A. Catalysts A through D show para-xylene selectivities of greater than 95% and show stable activity with no decline in toluene conversion with time under the toluene methylation reaction conditions (Table 5, FIGS. 1 and 2). Comparative Catalyst A shows a lesser conversion at all times as compared to Catalysts B through D, as shown in FIG. 1, whereas little to no difference is observed in the selectivity of Comparative Catalyst A and Catalysts B through D. In addition to the surprisingly improvement in conversion that occurs by adding the hydrogenating material just prior to forming, such a catalyst production method is economically attractive as it reduces the processing steps by eliminating an extra calcination step.

Comparative Catalyst E was made using the same P—ZSM-5, but contained no platinum. Table 5 and FIG. 2 shows that Comparative Catalyst E has a p-xylene selectivity of greater than 90%, but results in a decrease in both toluene conversion and p-xylene selectivity with time. Comparative Catalysts F and G were made from ZSM-5 (not phosphorus treated) and exhibit little or no decrease in toluene conversion with time but exhibit no para shape selectivity i.e., the catalysts make equilibrium concentration of p-xylene of only about 25% in the mixed xylene as shown in Table 5 and in FIG. 5.

The parent zeolites used for making Comparative Catalysts H and I were Beta zeolites having a $SiO_2/Al_2O_3$ mole ratio of 21 and 215, respectively. Beta zeolite has a three-dimensional pore structure having polymorphs A and B. Polymorph A has straight channels of 7.3 Å×6.0 Å and tortuous channels of 5.6 Å×5.6 Å and Polymorph B has straight channels of 7.3 Å×6.8 Å and tortuous channels of 5.5 Å×5.5 Å. Upon phosphorus treatment both Beta zeolite samples displayed reduced specific surface area and total pore volume. The Pt/P-Beta catalysts resulted in no para shape selectivity, as shown in Table 5 and in FIG. 5, yielding near equilibrium p-xylene concentration.

Comparative Catalysts J and K are Pt containing phosphorus treated Pt/Mordenite zeolite having SAR of 18 and 88, respectively. The pore structure of Mordenite zeolite consists of main channels with pore openings of 6.7 Å×7.0 Å and the channels are interconnected by side pockets with pore openings of 2.9 Å×5.7 Å having a free pore opening of 2.9 Å; this allows for only small molecules to freely move from one channel to another. The phosphorus treatment of the Mordenite caused significant reductions of specific BET surface area (see Table 3, 350 m$^2$/g for Mordenite, Sample 18, and 7 m$^2$/g for P-Mordenite, Sample 19; 442 m$^2$/g for Mordenite, Sample 21, and 24 m$^2$/g for P-Mordenite, Sample 22). Both Comparative Catalysts J and K resulted in no toluene conversion. Without being bound by theory, the Applicants believe that the reduction of surface area and pore volume together with no catalytic activity observed for Comparative Catalysts J and K may be associated with pore blockage by the phosphorus treatment of the zeolite.

Comparative Catalyst L is a Pt containing phosphorus treated Ferrierite zeolite catalyst. Similar to the ZSM-5 zeolite, Ferrierite contains a two-dimensional pore system comprising elliptical channels (5.5 Å×4.3 Å) intersected by channels of 8-membered ring structures (4.8 Å×3.4 Å), where the maximum diameter at the intersection of the channels is about 7 Å. Comparative Catalyst L shows no toluene conversion. Without being bound by theory, the Applicants believe that the smaller pore size of the Ferrierite zeolite may be associated with the lack of toluene conversion.

Table 5 summarizes the ratios of ethane/ethylene from catalytic results for Catalysts A through L. Catalysts A through D that were made using phosphorus treated ZSM-5 and that contain platinum have ethane/ethylene ratios of 0.3 to 0.5 suggesting the hydrogenation of byproduct ethylene produced during toluene methylation. Comparative Catalyst E, results in an ethane/ethylene ratio of about zero showing no hydrogenation activities. Comparative Catalysts F and G that contain platinum, but no phosphorus result in ethane/ethylene ratios of about 10 and about 3 for Comparative Catalysts F and G, respectively, suggesting that these catalysts have a higher hydrogenating activity than Catalysts A through D. These two catalysts though result in a low p-xylene selectivity of 27.3 and 27.4, respectively. Comparative Catalysts H and I show no or traces of ethane.

TABLE 5

| | | | | % Conv-Sel at 100 h* | | | |
| --- | --- | --- | --- | --- | --- | --- | --- |
| Catalyst | Zeolite | phosphorus treatment | platinum addition | Toluene Conversion | p-Xylene Selectivity | Ethane/Ethylene Ratio | Catalyst Deactivation |
| A | ZSM-5 (308) | P-treated | calcined Pt/P-ZSM-5, extruded | 7.0 | 97.1 | 0.39 | toluene conversion stable or increased |

TABLE 5-continued

| | | | | % Conv-Sel at 100 h* | | | |
| Catalyst | Zeolite | phosphorus treatment | platinum addition | Toluene Conversion | p-Xylene Selectivity | Ethane/Ethylene Ratio | Catalyst Deactivation |
| --- | --- | --- | --- | --- | --- | --- | --- |
| B | ZSM-5 (308) | P-treated | Pt downstream in the extruder | 9.2 | 96.8 | 0.48 | toluene conversion stable or increased |
| C | ZSM-5 (308) | P-treated | Pt downstream in the extruder | 10.4 | 96.2 | 0.37 | toluene conversion stable or increased |
| D | ZSM-5 (308) | P-treated | Pt downstream in the extruder | 9.5 | 97.5 | 0.31 | toluene conversion stable or increased |
| E | ZSM-5 (308) | P-treated | none | 5.8 | 93.7 | 0 | toluene conversion declined rapidly |
| F | ZSM-5 (308) | none | calcined Pt/ZSM-5, extruded | 12.2 | 27.0 | 8-12 | toluene conversion declined slowly |
| G | ZSM-5 (308) | none | Pt downstream in the extruder | 10.1 | 27.0 | 2-4 | toluene conversion stable or increased |
| H | Beta (21) | P-treated | Pt downstream in the extruder | 10.5 | 26.5 | a | toluene conversion declined rapidly |
| I | Beta (215) | P-treated | Pt downstream in the extruder | 5.3 | 26.0 | b | stable toluene conversion |
| J | Mordenite (18) | P-treated | Pt downstream in the extruder | none | | | |
| K | Mordenite (88) | P-treated | Pt downstream in the extruder | none | | | |
| L | Ferrierite (59) | P-treated | Pt downstream in the extruder | none | | | |

*Conv-sel estimated from plots of conversion and selectivity versus time on stream.
a No ethylene or ethane were present in product stream;
b No ethane, traces of ethylene present in product stream The method disclosed herein reduces the number of steps for catalyst preparation or formation. The process eliminates a step of adding hydrogenating material which is generally added to powder catalyst prior to forming shaped body or added to formed catalyst. In either case, the addition also requires a step involving heat treatment or calcination or decomposition of the hydrogenating compound. In the present disclosure the zeolite catalyst made using methods requiring reduced number of steps showed para shape selectivity. Such zeolite catalyst shows greater than 90% p-xylene selectivity for toluene methylation reaction (under the above conditions) with catalyst stability.

In an embodiment, a method of forming a catalyst for use in aromatic alkylation, comprises: treating a detemplated pentasil zeolite material with a phosphorus-containing compound to form a phosphorus treated zeolite; combining a hydrogenating material, the phosphorus treated zeolite, and a binder material to form a mixture; forming the mixture into a shaped body, wherein the mixture is formed into the shaped body without the mixture being heat-treated; and optionally calcining the shaped body to form the catalyst. Combining the hydrogenating material with the phosphorus treated zeolite and the binder material occurs prior to or during forming of the shaped body.

In another embodiment, a method of forming a catalyst for use in aromatic alkylation comprises: treating a detemplated MFI zeolite material with a phosphorus-containing compound to form a phosphorus treated zeolite; combining a hydrogenating material, the phosphorus treated zeolite, and a binder material to form a mixture; with no intervening calcining, forming the mixture into a shaped body; and calcining the shaped body to form the catalyst.

In another embodiment, a method of forming a catalyst, can comprise: combining a hydrogenating material, an active catalyst material, and a binder material to form a mixture; forming the mixture into a shaped body, wherein the mixture is formed into the shaped body without the mixture being heat-treated; and calcining the shaped body to form the catalyst; wherein the step of combining occurs prior to or during the step of forming. Optionally, the active catalyst material can be a zeolite (e.g., a beta zeolite, a mordenite zeolite, etc.), or a metal oxide (e.g., a mixed metal oxide), or a combination comprising at least one of the foregoing.

In another embodiment, a method of forming a catalyst for use in aromatic alkylation comprises: forming a mixture of a hydrogenating material, a phosphorus treated, detemplated, pentasil zeolite, and a binder material into a shaped body prior to decomposing the hydrogenating material to form a metal oxide; and calcining the shaped body to form the catalyst.

In the various embodiments: (i) the method further comprises, prior to the treating, removing a zeolite templating agent from as-synthesized zeolite by heating; and/or (ii) the zeolite can comprise a ZSM-5 zeolite; and/or (iii) the zeolite can have a $SiO_2/Al_2O_3$ molar ratio of 25 to 1,000; and/or (iv) the phosphorus-containing compound can comprise one or more of phosphoric acid, phosphorus acid, and ammonium hydrogen phosphate; and/or (v) the phosphorus content of the prepared catalyst is 1 to 15 weight % based on the total weight of zeolite; and/or (vi) combining the hydrogenating material with the mixture of the phosphorus treated zeolite and the binder material occurs prior to forming of the shaped body; and/or (vii) the hydrogenating material comprises a Group 10 transition metal; and/or (viii) the hydrogenating material comprises platinum; and/or (ix) the only hydrogenating material is a platinum compound; (x) the calcining occurs at a temperature of 250° C. to 550° C.; and/or (xi) the binder is alumina; and/or (xii) the binder content is 1 to 50 weight %; and/or (xiii) further comprising activating the catalyst prior to use at a temperature of 400° C. to 600° C. for a period of 0.5 to 5 hours under the flow of a reducing gas; and/or (xiv) the method further comprises, prior to the activating, drying the catalyst at a temperature of 100° C. to 300° C. for 0.5 to 3 hours under flow of a reducing gas of 50 to 500 cm$^3$/min; and/or (xv) the catalyst has greater than 90% para-xylene selectivity without declining toluene conversion; and/or wherein the active material is a metal oxide, a zeolite, or a combination comp.

Also disclosed herein are catalysts formed by any of the above methods, and methods of aromatic alkylation, comprising: contacting a stream comprising toluene with any of the above catalysts and alkylating the toluene to form para-xylene.

It should be understood that with respect to any concentration or amount range listed or described herein as being useful, suitable, or the like, it is intended to include every concentration or amount within the range, including the end points, and is to be considered as having been specifically stated. For example, "a range of 1 to 10" is to be read as indicating each and every possible number along the continuum between 1 and 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

As used herein, the term "ZSM-5" can also refer to ZSM-5-type zeolites that are isostructurally the same as ZSM-5 zeolite.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to differentiate one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

Any and all cited patents, patent applications, and other references are incorporated herein by reference in their entirety. However, if a term in the present application contradicts or conflicts with a term in the incorporated reference, the term from the present application takes precedence over the conflicting term from the incorporated reference.

While the disclosure has been described with reference to an exemplary embodiment, it will be understood by those skilled in the art that various changes can be made and equivalents can be substituted for elements thereof without departing from the scope of the disclosure. In addition, many modifications can be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

We claim:

1. A method of forming a catalyst for use in aromatic alkylation, comprising:
    treating a detemplated ZSM-5 zeolite material with a phosphorus-containing compound to form a phosphorus treated zeolite;
    combining a hydrogenating material, the phosphorus treated zeolite, and a binder material to form a mixture;
    forming the mixture into a shaped body, wherein the mixture is formed into the shaped body without the mixture being heat-treated; and
    calcining the shaped body to form the catalyst.

2. The method of claim 1, wherein the zeolite has a SiO$_2$/Al$_2$O$_3$ molar ratio of 25 to 1,000.

3. The method of claim 1, wherein the phosphorus-containing compound comprises one or more of phosphoric acid, phosphorus acid, and ammonium hydrogen phosphate.

4. The method of claim 1, wherein the phosphorus content of the prepared catalyst is 1 to 15 weight % based on the total weight of zeolite.

5. The method of claim 1, wherein the combining the hydrogenating material with the mixture of the phosphorus treated zeolite and the binder material occurs during forming of the shaped body.

6. The method of claim 1, wherein the hydrogenating material comprises a Group 10 transition metal.

7. The method of claim 1, wherein the hydrogenating material comprises platinum.

8. The method of claim 1, wherein the calcining occurs at a temperature of 250° C. to 550° C.

9. The method of claim 1, wherein the binder is alumina.

10. The method of claim 1, wherein the binder content is 1 to 50 weight %.

11. The method of claim 1, wherein the method further comprises activating the catalyst prior to use at a temperature of 400° C. to 600° C. for a period of 0.5 to 5 hours under the flow of a reducing gas.

12. The method of claim 11, where in the method further comprises, prior to the activating, drying the catalyst at a temperature of 100° C. to 300° C. for 0.5 to 3 hours under flow of a reducing gas of 50 to 500 cm$^3$/min.

13. A catalyst formed by the method comprising:
    treating a detemplated ZSM-5 zeolite material with a phosphorus-containing compound to form a phosphorus treated zeolite;
    combining a hydrogenating material, the phosphorus treated zeolite, and a binder material to form a mixture;
    forming the mixture into a shaped body, wherein the mixture is formed into the shaped body without the mixture being heat-treated; and
    calcining the shaped body to form the catalyst.

14. A method of aromatic alkylation, comprising:
contacting a stream containing an aromatic and a catalyst, wherein the catalyst is formed by the method comprising
treating a detemplated ZSM-5 zeolite material with a phosphorus-containing compound to form a phosphorus treated zeolite;
combining a hydrogenating material, the phosphorus treated zeolite, and a binder material to form a mixture;
forming the mixture into a shaped body, wherein the mixture is formed into the shaped body without the mixture being heat-treated; and
calcining the shaped body to form the catalyst;
and wherein the aromatic comprises toluene and
alkylating toluene to form para-xylene.

15. The method of claim 14, wherein the catalyst has para shape selectivity and the catalyst has no decrease in toluene conversion for at least 250 hours.

16. A method of forming a catalyst, comprising:
combining a hydrogenating material, an active catalyst material comprising a ZSM-5 zeolite, and a binder material to form a mixture;
forming the mixture into a shaped body, wherein the mixture is formed into the shaped body without the mixture being heat-treated; and
calcining the shaped body to form the catalyst.

\* \* \* \* \*